United States Patent [19]
Hartley, Jr.

[11] 3,934,274
[45] Jan. 27, 1976

[54] DEFLATABLE MAMMARY AUGMENTATION PROSTHESIS

[76] Inventor: John H. Hartley, Jr., 2915 Andrews Drive, NW., Atlanta, Ga. 30305

[22] Filed: Oct. 29, 1974

[21] Appl. No.: 518,399

[52] U.S. Cl. .............................. 3/36; 3/1; 128/462; 128/DIG. 21
[51] Int. Cl.[2] .... A61F 1/00; A61F 1/24; A41C 3/10
[58] Field of Search .............. 3/36, 1, 1.5; 128/462, 128/DIG. 21

[56] References Cited
UNITED STATES PATENTS

| | | | |
|---|---|---|---|
| 3,279,996 | 10/1966 | Long et al. | 3/1.5 X |
| 3,600,718 | 8/1971 | Boone | 3/36 |
| 3,663,968 | 5/1972 | Mohl et al. | 3/36 |

OTHER PUBLICATIONS

"Comparative Study of Cardiac & Vascular Implants in Relation to Thrombosis," by C. A. Hufnagel et al., Surgery, Vol. 61, No. 1, Jan. 1967, pp. 11–16.

Primary Examiner—Ronald L. Frinks
Attorney, Agent, or Firm—Jones, Thomas & Askew

[57] ABSTRACT

An implantable double walled tissue augmentation prosthesis consisting of a gel or liquid filled container within a liquid fillable container. A one-way flap valve is positioned within the wall of the liquid fillable container so that liquid may be selectively added to that container for inflation. Following implanting of the prosthesis, the liquid filled container may be deflated by removal of liquid therefrom to reduce any spherical contracture of the prosthesis caused by tissue contraction around the prosthesis. The prosthesis is most suitable for mammary augmentation.

9 Claims, 5 Drawing Figures

U.S. Patent  Jan. 27, 1976  3,934,274

DEFLATABLE MAMMARY AUGMENTATION PROSTHESIS

This invention relates to a tissue augmentation prosthesis which is particularly suited for mammary augmentation, and is more particularly concerned with an implantable prosthesis that may be inflated with liquid after implantation and subsequently deflated by removal of liquid to relieve the effects of spherical contracture of surrounding tissue on the prosthesis.

Mammary augmentation prostheses are normally divided into two general catagories: (1) the external prosthesis to be attached to or carried adjacent the outside of the body, as by carrying in a brassiere or the like; and (2) the implantable prosthesis that is surgically implanted beneath the skin of the body either between the chest wall and the mammary gland, as in the case of cosmetic augmentation or replacing the mammary gland following a mastectomy.

Prostheses designed for external use have been made of numerous materials and have included containers filled with various materials in an effort to provide a total effect similar to a normal human breast. Problems associated with the implanting of a prosthesis are not encountered with those prostheses designed for external application. Consequently, a wider latitude of design and implant material is available for such external application.

The implantable prosthesis on the other hand must meet certain rigid standards and requirements because of the implantation of the prosthesis beneath the skin of the patient. Silicone gel has been found to be a desirable material to approximate normal contours and tissue characteristics, but there have been problems in the use of silicone gel as a subcutaneous implantation. It has been determined to be objectionable and undesirable to inject silicone gel or fluid subcutaneously so that the gel or fluid itself is in contact with body tissue. Consequently, the gel has been placed within a silicone rubber container which retains the gel within the container and prohibits introduction of the gel into the body of the patient. While such a prosthesis when properly implanted effects augmentation of a breast, in time tissue surrounding the prostheses may contract and cause a spherical contracture of the prostheses into a relatively rigid and tense structure which is spherical in shape and relatively immovable, causing thereby a superior pole convexity of the upper surface of the breast and a firm, aesthetically undesirable breast. As the tissues around the implant contract, the fixed volume of the silicone gel material within its silicone rubber container is forced into a shape having the smallest possible surface area. The shape of the prosthetic implant becomes spherical thereby causing the breast to assume an abnormal spherical appearance with superior pole convexity. Once implanted it is not possible to remove a portion of the silicone gel material by insertion of a hypodermic needle through the breast of the patient and into the prosthesis because the silicone gel material is so thick, viscous and cohesive that it is not easily removed through the hypodermic needle. In addition puncture of the container for the gel by the needle would permit undesirable and objectionable leaking of the gel into the body of the patient.

Additionally, it has been determined that silicone gel feels slightly cooler to the touch than normal body temperature and therefore feels somewhat uncomfortable under certain circumstances when implanted beneath the skin.

The present invention overcomes the above mentioned and other problems with prior art implantable prostheses by providing a prosthesis which may be selectively enlarged prior to or during implant procedures and subsequently reduced in size following spherical contracture of the tissue surrounding the prosthesis. Enlargement of the prosthesis is obtained through the addition of saline solution or other suitable fluid to the prosthesis, such a solution being easily handled by conventional hypodermic syringe equipment.

These and other features and advantages of the present invention will become apparent from consideration of the following specification when taken in conjunction with the accompanying drawings in which.

Figure 1:
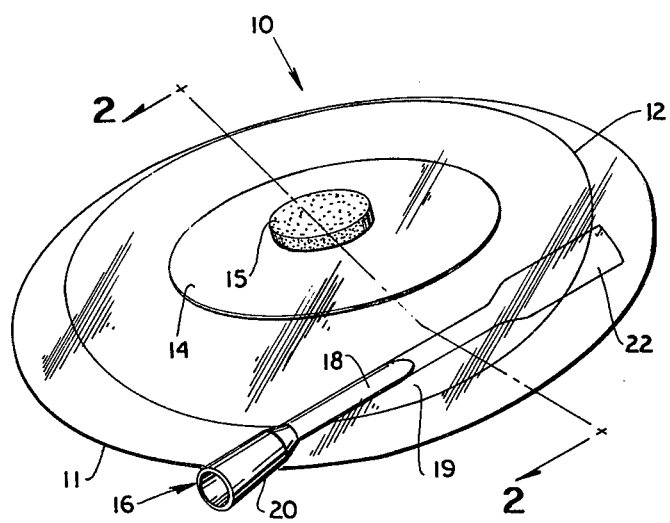
FIG. 1 is a perspective view showing the posterior side of a prosthesis made in accordance with the present invention.
Figure 2:
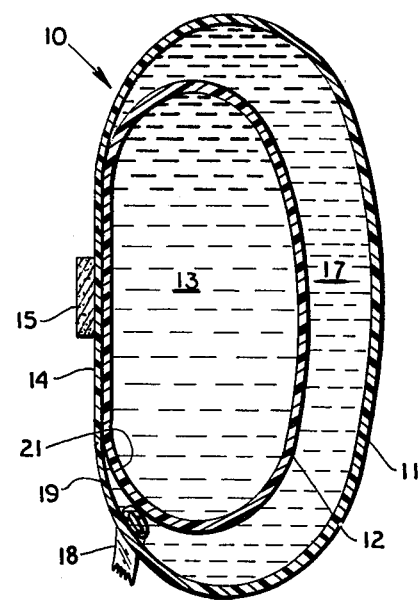
FIG. 2 is a cross-sectional view taken substantially along the line 2—2 in FIG. 1.
Figure 3:
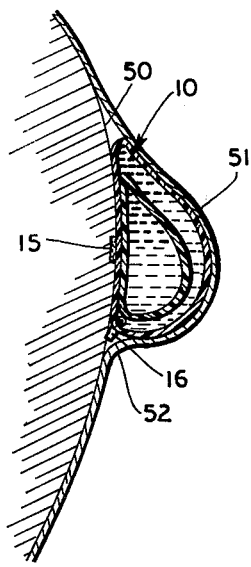
FIG. 3 is a somewhat schematic illustration showing a cross-sectional view of the prosthesis of FIG. 1 implanted in a patient.

Referring now to the drawings, and more particularly to FIGS. 1, 2 and 3, there is shown a surgically implantable mammary augmentation prosthesis comprising an outer sac 11 and an inner capsule 12 contained within the outer sac and occupying less than the entire volume of the outer sac. The volume of outer sac 11 is normally at least 75 cc and rarely more than 200 cc, but may be as low as 25 cc, this volume being in excess of the volume occupied by inner capsule 12. The walls of the sac and the capsule are constructed of a soft, flexible material such as silicone rubber compound. The walls of the inner capsule are impervious to the material 13 contained therein and retain the material within the capsule. The walls of the outer sac are semi-permeable and permit an exchange of fluid from within the sac to the tissue surrounding the prosthesis without loss of effective volume. According to one optional embodiment of the present invention, it is possible to place medication within the liquid contained in the outer sac and thereby achieve a long term continuous application of medication to the area surrounding the prosthesis. Of course, the walls of the outer sac may also be so thick that they are also impervious to all liquids but it is not necessary or critical that such wall thickness be present in the walls of the outer sac. The primary criterion for the walls of the present invention are that the inner capsule contain the material therein and that the complete prosthesis be soft, pliable and comfortable while also causing the prosthesis to assume natural body contours.

The walls of both the inner capsule and outer sac have a substantially flat rear wall and the capsule and sac in this embodiment are bonded together in a common area 14 along their rear walls to form a posterior side for the prosthesis. The front walls of the sac and capsule assume an outwardly convex shape closely approximating the shape of human breasts. Within the central portion of the posterior common area 14 of the prosthesis, there is a fixedly positioned attachment patch of open cell foam flexible plastic material 15. When in position following implant, tissue may grow into patch 15 to anchor the prosthesis in position. It should be understood that the presence of patch 15 is not required for the present invention since it is possible in some applications to delete patch 15 and achieve satisfactory results. The use of and need for anchor patches in augmentation prosthesis is well known to those of ordinary skill in this art and it is felt that further discussion of this element is unnecessary.

Capsule 12 is permanently filled completely with a high or low viscosity material 13 such as silicone gel as a high viscosity material or sterile saline solution as a low viscosity material to simulate the contours and characteristics of a human breast. Currently, silicone gel material is most popular for use in implantable mammary augmentation prostheses. However, it is recognized that other materials may be equally suitable so long as the consistency and viscosity of the implant material closely simulates the contours and characteristics of the human breast. Conventionally, mammary augmentation prostheses contain from 100 cc to 300 cc of silicone gel material. Of course, more or less such material could be employed if desirable.

Outer sac 11 is selectively filled with a relatively thin liquid 17 such as sterile, normal or isotonic saline solutions or other typical liquids which are compatible with the human body. Typically, from 75 to 125 cc of saline solution are injected into sac 11. It should be understood of course that more or less such solution could be used when desirable within the limits of the capacity of the sac. Filling of outer sac 11 is accomplished by means of filling valve 16. Valve 16 includes tube 18 which passes through and is sealed along its outer edges to posterior wall 19 of sac 11. Attached to the exterior end of tube 18 is funnel section 20 and attached to the inner end of tube 18 is a flap valve 22. Flap valve 22 is formed integrally with tube 18 and is quite flexible and soft to the touch. Flap valve 22 lies generally between the posterior wall 19 of sac 11 and the posterior wall 21 of capsule 12.

Funnel section 20 of valve 16 is provided for receiving a long cannula which is attached to the end of a syringe or other such liquid displacement device. The funnel and tube 18 aid in properly guiding the cannula into flap valve 22 to open the valve and allow liquid to be introduced through the cannula and into sac 11.

As shown in FIG. 3, when properly oriented beneath the skin 51 of the patient, the patch 15 of the prosthesis lies adjacent the chest wall 50 of the patient so that tissue may grow into the patch and anchor the prosthesis. Additionally, the prosthesis should be oriented so that valve 16 is in a lowermost posterior position so that the implant overlays the valve and aids in its concealment from sight and touch. Preceeding closure of the surgical incision beneath the augmented breast, the exterior portion of tube 18 containing funnel section 20 is cut from valve 16 to present a relatively smooth and attractive appearance to the posterior section of the prosthesis.

The procedure contemplated for implant of the prosthesis according to the present invention varies depending on whether the total procedure involves a mastectomy removal of breast tissue or simply mammary augmentation for cosmetic purposes. For the purpose of explanation the following discussion is based on mammary augmentation with no consideration being given to procedures or modifications necessary due to the performance of a mastectomy operation.

Following preparation of the patient, the implantation procedure includes marking the dissection line in the inframammary crease, making the incision and dissection and achieving hemostasis within the compartments formed between the mammary gland and the chest wall. Prior to insertion of the prosthesis 10 into the compartment, the competence of the sac 11 is tested by injecting a predetermined quantity of saline solution into the sac 11 through the valve 16. If it is found that the sac 11 is properly sealed, the saline solution is removed, and the prosthesis is placed into the compartment while the sac 11 is in a deflated condition.

After the prosthesis have been appropriately placed within the compartments (assuming bilateral mammaplasty), the sacs 11 are inflated by insertion of a cannula into valve 16 and injecting a predetermined quantity of liquid into sac 11. After the liquid (normally sterile saline solution) has been injected, the sac 11 is carefully checked and all air is removed, using the cannula and attached syringe. The cannula is then removed, the exterior portion of tube 18 is cut off as closely as possible to the wall of the sac 11, and the prosthesis is positioned within the compartment. The procedure is completed by appropriate suturing of the incision.

Following the implantation procedure, the patient has desirable mammary augmentation. The augmented breasts are soft and freely movable, closely simulating normal breast contour, appearance and feel. Also, the patient has desirable straight line fall from the intraclavicular area to the nipples of the breasts, and slight superior pole concavity of the upper surface of the breasts. If there is some hypertrophy in the surgical wound, it will not be signficantly noticeable since the surgical wound is along the inframammary crease.

During the six months after implantation of the prostheses, the tissue surrounding the prosthesis may contract, forcing the prosthesis to assume a somewhat spherical shape. This spherical contracture produces a rigidity in the breast along with unsightly superior pole convexity of the upper surface of the breast. With the prosthesis of the present invention, reduction in size of the prosthesis is easily accomplished by a relatively uncomplicated office procedure to decompress the implant and relieve the rigidity and convexity.

The decompression procedure involves evacuation of a portion or all of the solution from the outer sac 11. To do so, a skin anaesthetic is applied in the vicinity of the surgical wound, and a hypodermic needle is inserted through the patient's skin and into the sac 11. A syringe is used to evacuate a portion or all of the solution, and the needle is removed. Following decompression, a more normal appearance for the breast is achieved with no spherical contracture of the prosthesis.

Normally, decompression involves removal of all or substantially all of the solution with the sac 11. If any solution remains within the sac, it is possible that sac 11 may leak the remainder thereof through the needle puncture hole in its wall. Since sac 11 is filled with a sterile saline solution or other solution which is compatible with the human body, there is no harm or cause for concern because of such leakage.

It is recognized, however, that in some applications less than all the liquid within sac 11 will be removed during decompression of the prosthesis and no leakage will occur. Furthermore, it is also recognized that in many instances spherical contracture will be of such a small degree that decompression will not be necessary. In both of these circumstances, the presence of the solution within sac 11 will have an advantageous effect for the prosthesis. It is known that silicone gel presents a rather cold feel to the touch and under certain circumstances such a feel is undesirable. It has been found that the layer of saline solution effectively insulates the silicone gel and its capsule from contact with the patient's skin. In addition, it has been found that saline solution assumes a temperature more closely approximating that of human tissue and presents a feel which is more natural to the touch.

Though the present mammary prosthesis employs a liquid of a low viscosity, such as saline solution there will be very little, if any, noise or sloshing produced by agitation of the water. In order for a liquid such as the water within a saline solution to generate sound, there must be a shockwave transmitted through the liquid which causes the surface of the liquid to be agitated, thereby creating soundwaves. Referring to FIG. 2 of the drawings, it will be seen that a shockwave which might be created within the sac 11, as the sac is moved, will be transmitted across the sac 11 to engage the capsule 12. The material within the sac 12 would break-up the shockwave and aid in dissipating that energy before transmitting the energy of the shockwave to other sections of the sac 11 and the liquid therein.

Figure 4:
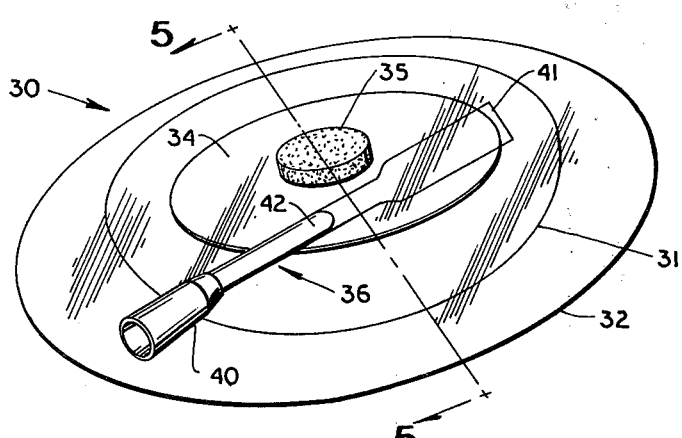
FIG. 4 is a view similar to FIG. 1 showing a modified form of the prosthesis according to the present invention.
Figure 5:
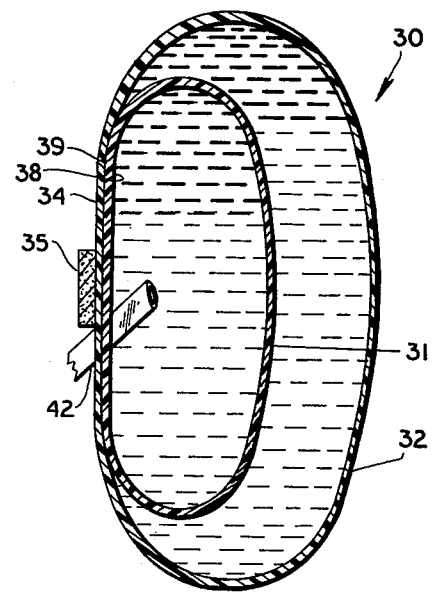
FIG. 5 is a cross-sectional view taken substantially along the line 5—5 in FIG. 4.

An alternative form of the present invention is demonstrated in FIGS. 4 and 5. This embodiment of the invention includes a prosthesis 30 that comprises an inner sac 31 for reception of a low viscosity liquid such as saline solution and an outer capsule 32 filled with a material of either high or low viscosity such as silicone gel as a high viscosity material and saline solution as a low viscosity material. As in the prosthesis 10, the sac and the capsule are bonded together along their posterior walls in a common area 34, the common area 34 having a substantially centrally located optional attachment patch 35.

In this embodiment, sac 31 is located within capsule 32 and the valve member 36 must pass through the posterior walls 38 and 39 of the sac and capsule respectively in the vicinity of the common area 34. The valve member 36 is substantially the same as the valve member 16 described in conjunction with the embodiment of the invention shown in FIGS. 1 and 2 and includes an outer funnel section 40 for receiving a cannula or the like and a flap valve 41 which is disposed within the sac 31.

The procedure for use of the prosthesis 30 is substantially the same as that described above for the prosthesis shown in FIGS. 1 and 2, except for the obvious difficulty in decompression. Puncturing of the capsule 32 would be objectionable and quite undesirable since the material within the capsule could leak out of the capsule. Consequently, a surgical incision is made to allow access to the posterior portion of sac 31. While this procedure is not as desirable as the simple decompression possible with the prosthesis 10, the resulting decompression through valve member 36 would reduce the undesirable aspects of spherical contracture of tissue surrounding the implant.

It will therefore be seen that the prosthesis of the present invention provides a means for augmentation of a hypoplastic breast, or for replacement of breast tissue in the case of a mastectomy operation. The prosthesis of the present invention provides the desired amount of augmentation by selection of the volume of the capsule and the volume of liquid injected into the sac.

It should be clearly understood that while the present prosthesis is particularly suitable for mammary augmentation, it is quite conceivable that other portions of the human body could be augmented to replace tissue losses or deficiencies. In the case of massive wounds to the musculature of arms and legs, it would be possible to rebuild those areas to more closely simulate normal body contours.

As a further alternative embodiment of the present invention it should be understood that the outer wall of sac 11 may be coated with medication prior to implant so that such medication would be available for immediate application to the tissues surrounding the prosthesis. An additional embodiment in this respect consists of incorporating medication into the structure of the outer wall of sac 11 so that the medication could migrate through the matrix of the material constituting the outer wall of the sac and evolve from the outer surface of the wall to be available for application to the tissues surrounding the prosthesis. It is contemplated that suitable medication would be incorporated into the construction material for the sac 11 during preparation of the construction material. The medication would be incorporated in such a fashion that the medication would remain mobile within the matrix of the construction material. The construction material, such as silicone rubber, would then be formed into sacs such as sac 11 and under the conditions existing within the human body, the medication would migrate through the matrix of the silicone rubber wall and be available for application to surrounding tissue from the surface of the wall. Such an application of medication would provide a method for long term treatment of areas of the body with appropriate medication.

In summary it should be understood that the present invention comprises an augmentation prosthesis for subcutaneous implantation beneath the skin of a patient. The prosthesis comprises an exterior sac and an interior capsule within the sac. The capsule is fixed to the rear wall of the sac and occupies less than the entire volume of the sac. The capsule, in the preferred embodiment, contains a soft material such as silicone gel and the sac is inflated with a liquid such as normal saline solution after implantation beneath the skin of a patient. The sac includes a discrete one-way valve means for selective addition of the liquid into the sac. The valve means is attached to a wall of the sac and fixed in position in that wall so that the valve will not move relative to said point of attachment in the wall. In an alternative embodiment, the sac of the prosthesis contains a soft material such as silicone gel and the inner capsule may be inflated with liquid after implantation of the prosthesis. In this embodiment the valve means is positioned in a wall of the capsule and is fixed against movement relative to the point of attachment with the wall. The valve means also extends through a wall of the sac so that liquid may be introduced into the capsule.

It will of course be understood that the particular embodiments of the invention here shown are by way of illustration only, and are meant to be in no way restrictive; therefore, numerous changes and modifications may be made and the full use of equivalents resorted to, without departing from the spirit or scope of the invention as defined by the appended claims.

I claim:

1. An augmentation prosthesis for subcutaneous implantation beneath the skin of a patient comprising an exterior sac containing an interior capsule which occupies less than the entire volume of the sac, said capsule being fixed to said sac and containing a fixed volume of soft material and said sac including a discrete one-way valve means for selective addition of a liquid into said sac, said valve means being attached to a wall of said sac and being fixed against movement relative to said wall at its point of attachment thereto, said liquid being compatible with the human body, whereby said augmentation prosthesis may be inserted into a cavity within the human body with substantially no liquid in said sac, liquid may be introduced into said sac through said valve means while the sac is positioned within the cavity, the cavity may be closed and liquid may be extracted from said sac by piercing the skin of the patient with a hypodermic needle and piercing the sac with the needle and withdrawing a quantity of liquid from said sac to reduce any compression of the sac by contracture of surrounding tissue.

2. Augmentation prosthesis of claim 1 wherein said sac and said capsule have posterior walls and a central portion of said posterior walls are fixed together.

3. Augmentation prosthesis of claim 2 wherein said valve means is located in the posterior wall of said sac and behind the posterior wall of said capsule.

4. Augmentation prosthesis of claim 1 wherein said soft material is silicone gel.

5. Augmentation prosthesis of claim 1 wherein the soft material contained in said capsule is a liquid.

6. Augmentation prosthesis of claim 1 wherein the sac includes a wall having an exterior surface and medication is coated on said exterior surface.

7. Augmentation prosthesis of claim 1 wherein the sac includes a wall having an exterior surface and medication is incorporated into the matrix of the construction material for said wall for migration through said matrix and exposure on said exterior surface.

8. Augmentation prosthesis of claim 1 wherein said capsule has a volume of from 100 to 300 cubic centimeters and said sac has a volume of 25 to 200 cubic centimeters in excess of the volume of the capsule.

9. An Augmentation prosthesis for subcutaneous implantation beneath the skin of a patient comprising an exterior sac containing an interior capsule which occupies less than the entire volume of the sac, said sac being fixed to said capsule and containing a fixed volume of soft material and said capsule including a discrete oneway valve means for selective addition of a liquid into said capsule, said valve means being attached to a wall of said capsule and being fixed against movement relative to said wall at its point of attachment thereto, said liquid being compatible with the human body, whereby said augmentation prosthesis may be inserted into a cavity within the human body with substantially no liquid in said capsule, liquid may be introduced into said capsule through said valve means while the capsule is positioned within the cavity, the cavity may be closed and liquid may be extracted from said capsule by piercing the skin of the patient with a hypodermic needle and piercing the capsule with the needle and withdrawing a quantity of liquid from said capsule to reduce any compression of the sac and capsule by contracture of surrounding tissue.

* * * * *